United States Patent [19]

Dielacher et al.

[11] 3,979,280

[45] Sept. 7, 1976

[54] SEPARATION OF UNSATURATED COMPOUNDS FROM LIQUID HYDROCARBON MIXTURES CONTAINING SAME

[75] Inventors: Maximilian Dielacher, Hamburg; Uwe Hansen, Jesteburg, both of Germany

[73] Assignee: Deutsche Texaco Aktiengesellschaft, Hamburg, Germany

[22] Filed: Dec. 12, 1974

[21] Appl. No.: 531,950

[30] Foreign Application Priority Data

Dec. 22, 1973   Germany............................. 2364306

[52] U.S. Cl. ..................... 208/310 R; 260/674 SA; 260/677 AD
[51] Int. Cl.² ........................................ C10G 25/02
[58] Field of Search............... 208/310; 260/674 SA, 260/677 AD

[56] References Cited

UNITED STATES PATENTS

| | | | |
|---|---|---|---|
| 2,449,402 | 9/1948 | Lipkin et al. ........................ | 208/310 |
| 2,865,970 | 12/1958 | Thomas........................... | 260/676 R |
| 3,409,691 | 11/1968 | Small ................................ | 208/310 |
| 3,922,217 | 11/1975 | Cohen et al..................... | 208/310 R |

*Primary Examiner*—Herbert Levine
*Attorney, Agent, or Firm*—T. H. Whaley; C. G. Ries; Robert Knox, Jr.

[57] ABSTRACT

Unsaturated hydrocarbons are separated from liquid mixtures containing same by adsorbing the unsaturated compound using a metal-loaded macroporous exchange resin and desorbing the unsaturated compound using a normally gaseous hydrocarbon.

11 Claims, 1 Drawing Figure

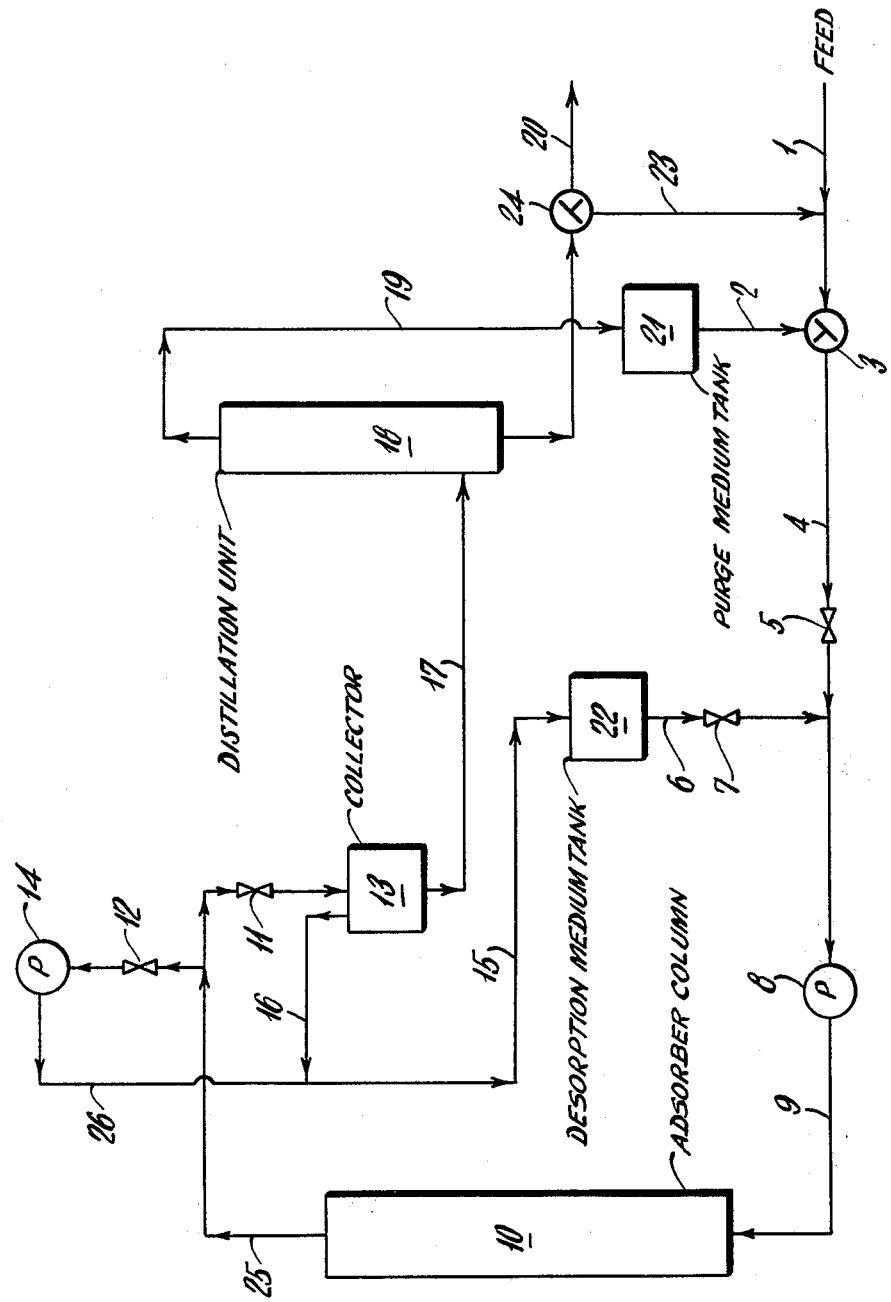

SEPARATION OF UNSATURATED COMPOUNDS FROM LIQUID HYDROCARBON MIXTURES CONTAINING SAME

The present invention relates to a process for the separation of unsaturated hydrocarbons from hydrocarbon mixtures by means of macroporous exchange resins wherein the unsaturated hydrocarbons are retained on the exchange resin by adsorption and are displaced therefrom in the liquid phase using a normally gaseous hydrocarbon.

The separation of hydrocarbon mixtures continues to be a matter arousing considerable interest particularly in mixtures composed of materials the separation of which, say by extractive distillation, can be performed only with difficulty when the physical and chemical differences between these materials are small. The application of techniques for the recovery of butadiene or aromatics from hydrocarbon mixtures by extraction or extractive distillation to, for example, the separation of monoolefins from their paraffinic counterparts 25 carbon atoms has been found to be unsatisfactory.

Another known method is the liquid-phase extraction, and subsequent recovery, of olefins with low carbon numbers from paraffin/olefin mixtures, using metal salt solutions, particularly solutions of Cu-(I) salts and Ag salts. However, these methods are for the most part confined to the separation of low carbon number olefins.

The separation of olefins from hydrocarbon mixtures by adsorption on molecular sieves. Generally, these processes are conducted at temperatures leading to a partial polymerization, or resinification, of the adsorbed olefin so that both the olefin yield and the capacity of the adsorbent are greatly diminished.

U.S. Pat. No. 2,865,970 discloses the use of a silver ion laden anion exchange resin for the removal of piperylene from n-heptane. In this process, the piperylene content of the treated n-heptane solution is reduced from 2 to 1 percent leading to the conclusion that the use of this technique for the separation of monoolefins would give unsatisfactory results. U.S. Pat. No. 3,409,691 proposes to separate polar organic materials from those less polar by sorption using a solid sorbent, namely, a dry macroporous cation exchange resin or a metal salt thereof having a specific surface area of at least 20 m² per gram. Among the polar organic materials separated from an aliphatic hydrocarbon, there have been mentioned alcohols, aldehydes, ketones, ethers, mercaptanes, chlorinated hydrocarbons, olefins and aromatic hydrocarbons.

German Offenlegungsschrift No. 2,156,075 discloses the purification of olefins by treating the olefins to be purified in the liquid phase with a solid cation exchange resin containing carboxyl groups, sulfonic acid groups or phosphoric acid groups in the form of an alkali salt or alkaline earth salt. The porous cation exchange resin which is used has a pore diameter of from $10^{1.3}$ to $10^5$ A and a specific surface area of at least 1 m² per gram.

It is an object of the present invention to provide a process permitting a quantitative and continuous separation of unsaturated hydrocarbons from hydrocarbon mixtures, said process constituting a further development of known separation methods.

We have found a process for the separation of unsaturated hydrocarbons from liquid hydrocarbon mixtures using macroporous cation exchange resins can be provided, wherein the physical-chemical properties of the mixture components differ only slightly or wherein only traces of the unsaturated compounds occur in the mixture, said separation process being conducted with metal ion laden cation exchangers having a specific surface area of at least 1 m²/gram and a pore width of greater than 10 A, said process being characterized in that the unsaturated compounds are adsorbed on macroporous dehydrated cation exchange resins laden with monovalent silver or copper ions and, subsequently, displaced therefrom in liquid phase, at temperatures of from 10° to 40°C and superatmospheric pressures of between 1 and 30 atmospheres, using a normally gaseous hydrocarbon.

According to our invention, sulfonated styrene-divinylbenzene copolymer type cation exchange resins are employed as adsorbents for the separation of unsaturated hydrocarbons from hydrocarbon mixtures, said cation exchange resins having specific surface areas and pore volumes ranging within defined limits which may be determined after the following pretreatment:

METHOD A

1. Twenty grams of cation exchange resin are suspended in 150 ml of distilled water at ambient temperature and stirred several times. Thereafter, the resin is allowed to settle, and supernantant water is decanted.
2. Step 1 is repeated with 200 ml of distilled water.
3. By means of a Buchner funnel the water-wetted resin is freed from adherent water and then predried under vacuum conditions for 10 minutes.
4. The pre-dried resin is vacuum dried in a porcelain dish for about 12 hours at about 80°C.

METHOD B

1. Thirty grams of cation exchange resin are pretreated according to Method A, Steps 1 through 3.
2. The so pretreated resin is transferred to a glass tube having an inside diameter of 2.54 cm closed at the bottom with a coarse fritted glass support, and successively eluted with 500 ml of pure methanol,
3. then with 500 ml of pure benzene and, finally, with
4. 500 ml of pure isooctane.
5. Thereafter, it is transferred to a porcelain dish and vacuum dried for about 12 hours at about 80°C.

After these pretreating steps the specific surface area of the resin samples is determined according to the BET method (cf. JACS 60 (1938), pp. 309 through 319 and 59 (1937), pp. 1553 through 1564 and 2682 through 2689). The pore volume is calculated as the difference between the grain and skeletal volumes, according to the mercury-water method. By grain volume is meant the volume of mercury displaced by 1 gram of the resin sample; by skeletal volume the amount of water displaced by 1 gram of the resin sample. Gel type resins have a specific surface area $s$ of < 1 m²/g, after pretreatment according to both Method A and Method B, whereas typical macroporous resins have specific surface areas $s_A >$ 1 m²/g and also $s_B >$ 1 m²/g. Similarly, pore volumes $v_A$ and $v_B$ of less than 0.10 ml/g/of resin, respectively, characterize gel type resins, and pore volumes $v_A$ and $v_B$ of greater than 0.10 ml respectively, characterize macroporous resins, after pretreatment by Method A and Method B.

Tests with gel type cation exchange resins gave unsatisfactory results in that the yields of separated unsaturated hydrocarbons were low and in some cases there was no separation from the saturated hydrocarbons.

Again, if the gel type cation exchange resins were laden with metal ions such Ag or Cu ions; it was found that a separation of unsaturated hydrocarbons from hydrocarbon mixtures containing saturated hydrocarbons took place only to a small extent. When the process was conducted continuously as is described below, this procedure did not result in any improvement in selectivity. Surprisingly, it has been found that when macroporous cation exchange resins laden with metal ions are employed the selectivity in the separation of hydrocarbon mixtures is particularly good and recovery of the unsaturated hydrocarbons which are adsorbed and then eluted with a normally gaseous hydrocarbon is greatly facilitated.

Gel type exchange resins have a pore volume of from about 0.003 to 0.004 cu. cm/cu. cm of resin, and a pore radius which is hardly measurable, whereas macroporous exchange resins have a pore volume of greater than 0.1 cu. cm/cu. cm of resin, a measurable pore radius and a large specific surface area. Satisfactory exchange resins include commercially available macroporous or macroreticular cation exchange resins such as "Amberlite XE-284" (sulfonated styrene-divinylbenzene copolymer) having an average pore diameter of from about 40 to 50 A, a pore volume of from 0.35 to 0.50 cu. cm/cu. cm, a specific surface area of from about 570 to 580 square meters per gram and an exchange capacity of 3.3 milligram-equivalent/gram (dry basis), or "Amberlyst-15" (sulfonated divinylbenzene crosslinked polystyrene resin) having an average pore diameter of about 270 A, and a specific surface area of from about 40 to 60 square meter/gram. Preferred cation exchange resins according to this invention are those having a specific surface area of from 40 to 1000 square meter/gram, preferably from 500 to 750 square meter/gram, and an average pore diameter of from 20 to 250A, preferably from 40 to 60A.

Metal ion laden cation exchange resins are advantageous, in particular because of the more severe fractionation and the more complete desorption associated therewith. As compared to the molecular sieves which have been used in the past, the macroporous cation exchange resins have the advantages of use at substantially lower operating temperatures, an improved separation of the hydrocarbon mixtures, the use of lesser amounts of eluant, and their applicability to many differently composed hydrocarbon feed mixtures. The use of normally gaseous hydrocarbons as eluant promotes desorption and simplifies the separation of eluted unsaturated hydrocarbons from the eluant. Furthermore, it is possible to carry out the separation of the unsaturated hydrocarbons from hydrocarbon mixtures in simple manner in a continuous process as distinguished from the prior art batch type process.

Suitable metal ions include those derived from the elements of Groups IB through IVb, Ia and VIa through VIIIa of the Periodic System such as sodium, rhenium, platinum, cobalt, silver, copper, mercury, thallium or lead. The metal ions of silver, sodium, cobalt, copper or thallium are preferred. The elements preferably should be in an oxidized condition such that the ions are sufficiently fixed on the exchange resin structure and are not rinsed off during operations. The exchange resin is laden with ions in such an amount that, preferably, substantially all of the hydrogen ions are replaced. The hydrogen ions may be replaced by metal ions in known manner.

The process of this invention may be employed for the separation and recovery of unsaturated hydrocarbons from hydrocarbon mixtures. In particular, the process is applicable to the separation of hydrocarbon mixtures which are liquid under normal conditions, preferably for separating those mixtures into components which due to their small physical-chemical differences are practically inseparable by the usual separation techniques of distillation, extraction or extractive distillation, or whose separation would result in unproportionately high costs. Thus, the process of this invention is applicable to the separation of mixtures also comprising other hydrocarbons beside unsaturated. It may be used especially for separating mono-olefins from hydrocarbon mixtures, for example, mixtures of hydrocarbons with 10–20C atoms used as starting materials for detergents, are separated. These $C_{10-20}$ mixtures contain saturated and unsaturated compounds. Thus, even those olefins resulting from catalytic dehydrogenation can be separated from a $C_{10-14}$ n-paraffin mixture without requiring a fractionation by distillation into narrower carbon number cuts prior to the separation.

One embodiment of the method of this invention is illustrated in the accompanying drawing:

After filling the column 10 with cation exchange resin, valves 7 and 12 are closed, valves 5 and 11 are opened, three-way valve 3 is set so as to permit the feed mixture to pass therethrough, and pump 8 is switched on. The cation exchange resin is loaded to saturation with the unsaturated hydrocarbons, and then the three-way valve 3 is adjusted so as to permit passage of the purge medium from line 2. After the saturated nonadsorbed hydrocarbons have been displaced completely from the exchange column by the purge medium, valves 5 and 11 are closed and valve 7 is opened. At about 20°C, a certain pressure caused by the characteristic pressure of the normally gaseous desorbing agent builds up in the system. During the desorption step in which the unsaturated hydrocarbons are displaced from the exchange resin, valve 11 is opened, the opening being controlled so as to adjust a pressure depending on the desorbing agent in the system. The various fractions such as saturated higher-boiling hydrocarbons and desorbing agent are transferred from the collector 13 through line 17 to a distillation unit 18 where they are separated by distillation. The purge medium is passed overhead through line 19 to the purge medium tank 21. The saturated hydrocarbons are withdrawn from the bottom of unit 18 through line 20, or intermediate fractions containing unsaturated hydrocarbons are recycled through line 23 to the feed mixture. As soon as valve 11 discharges unsaturated hydrocarbons and purge and desorption media, the desorption medium is passed overhead from collector 13 through lines 16 and 15 to the desorption medium reservoir 22, and purge medium and displaced unsaturated hydrocarbons are transferred via line 17 to the distillation unit 18. Purge medium is withdrawn overhead and passed through line 19 to the purge medium tank 21. The purge unsaturated hydrocarbons are withdrawn through line 10 from the bottom of the unit 18. After completion of the desorption step, valve 7 is closed and pump 8 switched off. Valve 11 now is opened completely so that all of the liquid desorption agent evaporates from the system and is passed through lines 16 and 15 to the desorption medium reservoir 22. Valve 11 is closed and valve 12 opened and by applying vacuum by means of pump 14 any desorbing agent adherent to the exchange resin is removed therefrom and sent to tank 22 through line 26 and 15. Subsequently, the cycle is restarted by loading the exchange resin anew with fresh feed mixture.

The process of this invention is characterized mainly by four steps:

1. Adsorption of olefins on exchange resin with simultaneous elution of pure paraffins, which are provided, for example, for the further dehydrogenation.
2. Purging the loaded exchange resin with a saturated hydrocarbon. The olefin-paraffin fractions occurring after the removal of the solvent are recycled to the adsorption zone.
3. Desorption of olefins of high purity.
4. Removal of the desorbing agent at reduced pressure.

The feed in the column is purged with a light hydrocarbon. It is advantageous to use lower paraffin hydrocarbons having frm 5 to 10 carbon atoms such as hexanes, heptanes or octanes. According to the invention, the agents for desorbing the unsaturated hydrocarbons sorbed on the exchange resin are normally gaseous hydrocarbons, butenes or propene being preferred. Propene has an advantage over butenes in that it is more easily desorbed. However, with the use of propene, higher pressures throughout the system or more cost and equipment for cooling purposes are required. The process is conducted at temperatures in the range of from 10° to 40°C, preferably from 10° to 25°C, and under superatmospheric pressures of between 1 and 30 atmospheres, preferably 1 to 15 atmospheres.

EXAMPLE 1

In a 50 g sample of resin amberlite XE-284 the hydrogen ions were replaced by silver ions. For this purpose, $AgNO_3$ solution was introduced into a column packed with the resin ($H^+$ form) and the flow of $AgNO_3$ solution was continued until the effluent showed the same $Ag^+$ concentration as the solution. After the excess silver ions had been removed by rinsing with water, dehydration with n-heptane was carried out in a water separator.

Eighty ml ($\approx$60 g) of the activated resin in the silver form (26.8 wt. % Ag based on dry resin) was charged to the adsorption zone of the above described apparatus. The feed mixture to be separated was a n-$C_{12}$ olefin-paraffin mixture having 10 wt. % olefin (of which 88% were present in $\alpha$-olefin form)

| purge medium: | n-hexane |
|---|---|
| desorption medium: | n-butene |
| flow rate: | 65 ml/hr |
| operating temperature: | 20°C |

Each of the adsorption, purge and desorption steps was carried out three times.

TABLE 1

| Cycle | loading of resin in % $\frac{g\ olefin}{g\ resin} \cdot 100$ | purity of desorbed olefins in % |
|---|---|---|
| 1 | 7.1 | 93.1 |
| 2 | 6.0 | 78.1 |
| 3 | 6.3 | 89.2 |

EXAMPLE 2

This example was conducted as in Example 1, using the same apparatus and adsorption resin packing. As charge an n-$C_{12}$ olefin-paraffin mixture containing 10 weight percent of olefin (of which 94.8 percent were present as internal olefins) was employed.

TABLE 2

| Cycle | loading of resin in % $\frac{g\ olefin}{g\ resin} \cdot 100$ | purity of desorbed olefins in % |
|---|---|---|
| 1 | 7.0 | 85.0 |
| 2 | 5.0 | 72.0 |
| 3 | 6.0 | 92.0 |
| 4 | 5.0 | 90.0 |
| 5 | 4.6 | 88.0 |
| 6 | 5.8 | 74.0 |
| 7 | 4.9 | 82.0 |
| 8 | 5.6 | 86.0 |

EXAMPLE 3

This is a comparative example using 13X molecular sieve (in $Ag^+$ form) in comparison with Example 2. 75 ml (66 grams) of 13X molecular sieve in the silver form (36.1 weight percent Ag based on dried molecular sieve), which had been treated in known manner with a 50% $AgNO_3$ solution and, after drying, had been calcined for three hours at 450°C, was charged to the above described apparatus. The feed mixture was an n-$C_{12}$ olefin-paraffin mixture containing 10 weight percent olefin (94.8 wt. % of which were present as internal olefins). The test conditions were the same as those employed in Examples 1 and 2.

TABLE 3

| Cycle | loading of molecular sieve in % $\frac{g\ olefin}{g\ molecular\ sieve} \cdot 100$ | purity of desorbed olefins in % |
|---|---|---|
| 1 | 5.7 | 85.0 |
| 2 | 1.2 | 77.0 |
| 3 | 1.0 | 72.0 |
| 4 | 1.3 | 73.0 |
| 5 | 0.9 | 65.0 |
| 6 | 1.6 | 82.0 |
| 7 | 1.1 | 61.0 |
| 8 | 0.5 | 54.0 |

By comparing Examples 2 and 3 it is evident that under the same conditions both the loading of the adsorbent and the purity of the separated olefins are considerably lower when a molecular sieve is used as the adsorbent.

So far as is known, all of the processes which have been published so far and which employ molecular sieves as the adsorbent for the separation of olefins from hydrocarbon mixtures are operated under substantially more severe conditions. This involves higher stress on the adsorption material and, hence, greater wear of same; moreover, when the process conditions are more severe, this will lead to side reactions, which in the case of olefins would mean increased polymer formation and, hence, blocking of the active surface area.

EXAMPLE 4

The procedure, apparatus and adsorption resin packing (80 ml) as in Example 1 were used. The charge was a decane-pseudocumene mixture (1.0 weight percent of pseudocumene). The test run included four consecutive cycles.

TABLE 4

| Cycle | loading of resin with pseudocumene in % $\frac{\text{g pseudocumene}}{\text{g resin}} \cdot 100$ | purity of desorbed pseudocumene, in % |
|---|---|---|
| 1 | 6.5 | 92.5 |
| 2 | 5.6 | 88.4 |
| 3 | 5.2 | 94.5 |
| 4 | 5.5 | 90.3 |

The embodiments of the invention in which an exclusive property or privilege is claimed are defined as follows:

1. In a process for the separation of unsaturated compounds from liquid hydrocarbon mixtures containing same by contacting the mixture with a metal ion laden cation exchange resin having a specific surface area of at least 1 m²/g and an average pore diameter of greater than 10 A, the improvement which comprises adsorbing said unsaturated compounds on a macroporous dehydrated cation exchange resin laden with monovalent silver or copper ions and subsequently displacing said unsaturated compounds in liquid phase from said resin at a temperature between about 10° and 40°C. and a pressure between about 1 and 30 atmospheres using a normally gaseous olefin as the desorption medium.

2. A process according to claim 1, characterized by using cation exchange resins having a specific surface area greater than 40 m²/gram and an average pore diameter of lesser than 250 A.

3. A process according to claim 1 characterized by using propene or butene as the normally gaseous olefin.

4. A process according to any of claim 1 characterized by operating in a temperature range of from 10° to 25°C and under superatmospheric pressures of between 1 and 5 atmospheres.

5. A process according to claim 1 characterized by separating monoolefins having from 4 to 25 carbon atoms as the unsaturated compounds from hydrocarbon mixtures containing saturated hydrocarbons having from 4 to 25 carbon atoms.

6. A process according to claim 1 characterized by separating aromatics as the unsaturated compounds from hydrocarbon mixtures containing saturated hydrocarbons.

7. A process according to claim 3 characterized by operating at a temperature between 10° and 25°C and a pressure between 1 and 5 atmospheres.

8. A process according to claim 3 characterized by using a cation exchange resin having a specific surface area between 500 and 750 square meter/gram and an average pore diameter between 40 and 60A.

9. A process according to claim 4 characterized in that the resin is loaded with silver ions.

10. A process according to claim 4 characterized in that the resin is loaded with copper ions.

11. A process according to claim 1 characterized in that the resin is a sulfonated divinyl benzene cross-linked polystyrene resin.

* * * * *